(12) United States Patent
Wolleschensky et al.

(10) Patent No.: US 8,704,196 B2
(45) Date of Patent: Apr. 22, 2014

(54) COMBINATION MICROSCOPY (75) Inventors: Ralf Wolleschensky, Jena (DE); Ingo Kleppe, Jena (DE); Gerhard Krampert, Jena (DE); Michael Kempe, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 109 days.

(21) Appl. No.: 13/127,427

(22) PCT Filed: Oct. 28, 2009

(86) PCT No.: PCT/EP2009/007693
§ 371 (c)(1),
(2), (4) Date: Jul. 20, 2011

(87) PCT Pub. No.: WO2010/060515
PCT Pub. Date: Jun. 3, 2010

(65) Prior Publication Data
US 2011/0284767 A1 Nov. 24, 2011

(30) Foreign Application Priority Data
Nov. 3, 2008 (DE) .......................... 10 2008 054 317

(51) Int. Cl.
*G01J 1/58* (2006.01)
(52) U.S. Cl.
USPC ...................................... 250/458.1
(58) Field of Classification Search
USPC .......................................... 250/458.1, 459.1
See application file for complete search history.

(56) References Cited

U.S. PATENT DOCUMENTS

| 5,481,401 | A | 1/1996 | Kita et al. |
| 5,731,588 | A | 3/1998 | Hell et al. |
| 5,866,911 | A | 2/1999 | Baer |
| 6,072,625 | A | 6/2000 | Kitahara et al. |
| 6,633,432 | B2 | 10/2003 | Iketaki |
| 6,738,189 | B1 | 5/2004 | Ulrich et al. |
| 6,909,105 | B1 | 6/2005 | Heintzmann et al. |
| 6,924,490 | B2 | 8/2005 | Natori |
| 7,626,695 | B2 | 12/2009 | Betzig et al. |
| 7,880,150 | B2 | 2/2011 | Hell et al. |
| 7,894,067 | B2 | 2/2011 | Hell |
| 2003/0081209 | A1 | 5/2003 | Takahashi et al. |
| 2006/0038993 | A1 | 2/2006 | Hell |
| 2007/0023686 | A1 | 2/2007 | Wolleschensky et al. |

(Continued)

FOREIGN PATENT DOCUMENTS

| DE | 34 36 167 A1 | 4/1986 |
| DE | 44 16 558 A1 | 8/1995 |

(Continued)

*Primary Examiner* — Mark R Gaworecki
(74) *Attorney, Agent, or Firm* — Patterson Thuente Pedersen, P.A.

(57) ABSTRACT

A method for generating an image of a sample by a microscopy method including varying local resolution, wherein at least two of the following microscopy methods are combined: laser scanning microscopy, a microscopy method wherein the sample is excited to luminescence by structured line or wide area illumination, and a first microscopy image is generated from the images thus obtained, having increased local resolution greater than the optical resolution of the image, a further microscopy method according to the PAL principle, by which a second microscopy image is generated, indicating geometric locations of marker molecules emitting luminescent radiation at an increased local resolution relative to the optical resolution, and a further microscopy method, wherein the sample is marked using marking molecules suitable for the STED, ESA, or RESOLFT technique, and a third microscopy image is generated of STED, ESA, or RESOLFT, wherein the obtained images are superimposed.

19 Claims, 3 Drawing Sheets

(56) References Cited

U.S. PATENT DOCUMENTS

| | | |
|---|---|---|
| 2007/0206278 A1 | 9/2007 | Dyba et al. |
| 2008/0088920 A1 | 4/2008 | Wolleschensky |
| 2009/0250632 A1 | 10/2009 | Kempe et al. |
| 2009/0294694 A1 | 12/2009 | Lippert |
| 2010/0276608 A1 | 11/2010 | Liu et al. |
| 2011/0036996 A1 | 2/2011 | Wolleschensky et al. |

FOREIGN PATENT DOCUMENTS

| | | |
|---|---|---|
| DE | 196 54 208 A1 | 6/1998 |
| DE | 103 25 460 A1 | 11/2004 |
| DE | 10 2004 034 9998 A1 | 2/2006 |
| DE | 10 2005 034 443 A1 | 2/2007 |
| DE | 10 2006 009 831 A1 | 9/2007 |
| DE | 10 2006 021 317 B3 | 11/2007 |
| DE | 10 2006 046 369 A1 | 4/2008 |
| DE | 10 2006 047 912 A1 | 4/2008 |
| DE | 10 2006 060 180 A1 | 6/2008 |
| EP | 1 157 297 B1 | 11/2002 |
| EP | 1 907 826 B1 | 8/2009 |
| JP | 2003-130866 | 5/2003 |
| JP | 2007-17930 | 1/2007 |
| WO | WO 2006/127692 A2 | 11/2006 |
| WO | WO 2008/021834 A2 | 2/2008 |

COMBINATION MICROSCOPY

PRIORITY CLAIM

The present application is a National Phase entry of PCT Application No. PCT/EP2009/007693, filed Oct. 28, 2009, which claims priority from German Application Number 102008054317.9, filed Nov. 3, 2008, the disclosures of which are hereby incorporated by reference herein in their entirety.

FIELD OF THE INVENTION

The invention relates to a method and a microscope for the microscopy of a sample, wherein several microscopy methods differing in their resolution are combined.

BACKGROUND

The examination of samples by means of microscopy is a broad technical field for which there are varied technical solutions. Starting from the standard light microscopy, widely different microscopy methods have evolved.

A standard field of use of light microscopy for examining biological preparations is luminescence microscopy. In this process, particular dyes (so-called phosphors or fluorophores) are used for the specific tagging of samples, e.g. of cell parts. The sample is, as mentioned, illuminated with excitation radiation and the luminescence light excited thereby is recorded by suitable detectors. For this, a dichroic beam splitter is usually provided in the light microscope in combination with block filters which split the fluorescence radiation from the excitation radiation and enable a separate observation. Through this procedure, the imaging of individual, differently coloured cell parts in the light microscope is possible. Of course, several parts of a preparation can also be simultaneously coloured with different dyes attaching specifically to different structures of the preparation. This method is called multiple luminescence. Samples which luminesce per se, thus without added tagging substance, can also be surveyed.

Here, luminescence is understood, as is generally usual, as a generic term for phosphorescence and fluorescence, thus covers both processes.

To examine samples, it is also known to use laser scanning microscopy (also LSM for short) which, from a three-dimensionally illuminated image, reproduces by means of a confocal detection arrangement (when it is called a confocal LSM) or a non-linear sample interaction (so-called multiphoton microscopy) only that plane which is located in the focal plane of the objective. An optical section is produced and the recording of several optical sections at different depths of the sample then allows the generation, with the help of a suitable data-processing device, of a three-dimensional image of the sample which is composed of the different optical sections. Laser scanning microscopy is thus suitable for examining thick preparations.

Of course, a combination of luminescence microscopy and laser scanning microscopy is also used, in which a luminescent sample is imaged at different depth levels with the help of an LSM.

Laser scanning microscopes are also supplied as retrofit modules for normal light microscopes which then also enable a laser scanning microscopy of samples in addition to a normal microscopy. Like standard microscopy, laser scanning microscopy, and in particular laser scanning microscopy of luminescent samples, is also characterized by the optical resolution limit of the microscope used. However, laser scanning microscopy allows a very much higher depth of field, although with both microscopes the optical resolution is diffraction-limited by physical laws.

Different approaches have recently been developed for resolutions beyond the diffraction limit. These microscopy methods are characterized by the fact that they provide the user with a higher lateral and/or axial optical resolution compared with the standard microscope. In this description, such microscopy methods are called high-resolution microscopy methods, as they achieve a resolution beyond the optical diffraction limit. Diffraction-limited microscopes, on the other hand, are called standard microscopes. They realize known optical wide-field microscopy or laser scanning microscopy.

The gain in resolution with high-resolution microscopy is at the cost of a lower measuring speed, a smaller measuring field, as well as limitations in respect of the penetration depth and the tagging substances that can be used for the luminescence microscopy.

Thus, high-resolution microscopy methods can be used only for particular examinations, because of the essential compromises in respect of sample preparation and acquisition parameters (in particular acquisition speed, etc.). This is particularly awkward if it is wished to examine smaller areas in a large sample or to track a temporal development of a sample which proceeds at varying speeds.

SUMMARY OF THE INVENTION

An object of the invention is therefore to provide a microscope or a method for microscopy with which the previous design and use conflicts which accompany high-resolution microscopy are remedied.

This object is achieved according to the invention by a method for generating an image of a sample by means of microscopy methods which realize different spatial resolutions, wherein at least two of the following microscopy methods are combined: a first microscopy method in which the sample is excited to luminescence by structured line or wide-field illumination, the structuring is rotated and shifted several times for each rotation position, wherein at least three rotation positions and at least three shift positions per rotation position are realized, in each case the luminescent sample is imaged onto a 2D detector with a predetermined optical resolution and a first microscopy image with spatial resolution increased beyond the predetermined optical resolution is generated from the thus-obtained images by a computational processing comprising Fourier analysis, a second microscopy method in which the sample is labelled with label molecules which can be excited to emit particular luminescence radiation only after being activated by a switching signal, the switching signal is applied to the sample such that only a sub-set of the label molecules present in the sample are activated, wherein there are partial areas in the sample in which activated label molecules have a distance to their closest neighbouring activated label molecules which is greater than or equal to the predetermined optical resolution, the activated molecules are excited to emit luminescence radiation, the sample emitting luminescence radiation is imaged onto the 2D detector with the predetermined optical resolution, the image is analyzed and image data are generated from it which give the geometric locations of the label molecules emitting luminescence radiation with a spatial resolution increased above the optical resolution, and a second microscopy image is generated from the image data, a third microscopy method for generating a third microscopy image by means of laser scanning microscopy, a fourth microscopy method in which the sample is tagged with tagging molecules suitable for the STED, ESA or RESOLFT technique and a fourth microscopy image is generated by means of STED, ESA or RESOLFT, wherein the at least two obtained microscopy images are superimposed to form a composite image.

The object is further achieved by a combination microscope, formed for the microscopy of a sample with at least two microscopy methods differing in their resolution, wherein the microscope has: an objective which records the sample for all microscopy methods, a detection beam path and at least one illumination beam path which both at least partially coincide and pass through the objective, a microscope module connected to the detection beam path which has a tube lens and a 2D detector and, together with the objective, images the sample onto the 2D detector, a wide-field illumination module connected to the illumination beam path for the wide-field illumination of the sample through the objective, wherein the wide-field illumination module can be driven to emit illumination radiation in at least two different wavelength ranges, and an illumination radiation modulator which is downstream of the wide-field illumination module in illumination direction in the illumination beam path and which can be controllably activated and de-activated in the illumination beam path and imposes a stripe modulation in the activated state of the illumination radiation, wherein the illumination radiation modulator can be driven such that the stripe modulation can be shifted perpendicular to an optical axis of the illumination beam path, and wherein a controllable rotation device is further provided with which either the stripe modulation is rotatable about the optical axis of the illumination beam path or ray beams that have passed through the activated illumination radiation modulator and are thereby provided with the stripe modulation are rotatable in the illumination beam path about the optical axis of the illumination beam path, and a control device which is connected to the microscope module, the wide-field illumination module, the illumination radiation modulator and the rotation device and drives the microscope into different operating modes, wherein the control device is formed to activate the illumination radiation modulator in a first operating mode and to drive it together with the rotation device as well as to read the area detector and to process data delivered by the latter, in order to carry out the first microscopy method mentioned above, and is formed to de-activate the illumination radiation modulator in a second operating mode and to drive the wide-field illumination module successively to emit the illumination radiation in the at least two different wavelength ranges as well as to read the area detector and to process data delivered by the latter, in order to carry out the second microscopy method mentioned above.

The invention thus presents a combination, previously not yet realized or described in the state of the art, of particular high-resolution microscopy methods with standard microscopy methods. It is thereby possible to image comparatively small sample field sections (also called region of interest, or ROI) in high resolution and still supplement these with standard microscopy acquisitions or thus reveal them. Measurement cycles in high-resolution microscopy are also simplified by using data from the standard microscopy method, or increase the quality of the data which are obtained with their high-resolution microscopy methods.

Different high-resolution microscopy methods already known for themselves alone in the state of the art can be combined with laser scanning microscopy or with one another for the invention.

A high-resolution method relevant within the framework of the invention is described in U.S. Pat. No. 5,866,911 the disclosure of which in this respect may be incorporated here entirely. A light radiation having two wavelengths is used to increase resolution. The light radiation of one wavelength is focused as excitation light beam by means of an objective onto the sample to be measured, where it excites luminescence, fluorescence here. The increase in the spatial resolution now takes place because a light beam with the other wavelength depopulates the fluorescent state excited by the excitation light beam in partial areas. This light beam is therefore also called "depopulation radiation". The radiation now takes place e.g. such that the main maximum of the depopulation light beam and the main maximum of the excitation light beam partially overlap. Through this "de-excitation" of the sample at the edges of the area illuminated with excitation radiation, only a reduced volume still emits fluorescence. The resolution is consequently increased by this volume reduction.

Several mechanisms can effect such a depopulation, such as are for example described in DE 4416558 C2, U.S. Pat. No. 6,633,432 or DE 10325460 A1. They can all be used here.

An example is de-excitation by stimulated emission (STED). An excitation radiation excites a fluorophore. A depopulation of the thus-excited state is effected towards the ground state by light radiation with a wavelength in the range of the fluorescence wavelength. This stimulated emission has a wavelength which almost identically corresponds to that of the luminescence. The excitation wavelength is thus shorter, by the amount of the Stokes shift, than that of the depopulation radiation. The increase in resolution according to this approach thus uses two different light sources, as is also shown by DE 4416558 C2, the disclosure of which relevant to this is here incorporated in full by reference.

A further possible process of depopulation for the excited level is an excitation at a still higher state which can no longer emit luminescence. This lifting is called excited state absorption, which is why this procedure is also abbreviated to ESA. A corresponding description of this process can be found for example in U.S. Pat. No. 6,633,432, also incorporated by reference here. As the distance between the energy states in a sample or a dye decreases at higher states, a light source with less energy and thus a longer wavelength than for the excitation is used for the depopulation in the ESA process. Two different wavelengths, thus e.g. light sources, are used again.

So-called reversible saturable optical fluorescence transition (RESOLFT) which is described e.g. in DE 10325460 A1, also incorporated in full by reference, represents a further method for the depopulation for the fluorescence. For the spatially high-resolution imaging, this microscopy method uses a tagging substance which can be repeatedly transformed with the help of a switching beam from a first state in which fluorescence takes place into a second state in which the dye does not fluoresce, wherein the dye can return from the second state to the first state. The sample is transferred in partial areas with the switching beam into the second state, wherein a defined area of the sample is omitted. Fluorescence light is then excited with an excitation beam and subsequently recorded. The fluorescence light then originates only from sample volumes which have not previously been acted on by the switching beam. Through suitable overlapping of excitation beam and switching beam, the volume from which fluorescence light is emitted is smaller than allowed a priori by the resolution of the excitation beam and the sharpness of the zero point of the switching beam. A development of this high-resolution microscopy method is described in EP 1907826, which is also incorporated by reference here in full in this respect. There the demands on the necessary radiation sources are simplified by using suitable dyes. Here, a non-linearity of the excitation behaviour of the dye is exploited for the depopulation, whereby radiation on one wavelength can be saved.

In all three of the named high-resolution microscopy methods, fluorescence is thus prevented by using light radiation with a wavelength which is not the same as the wavelength for the excitation. At the same time, this light radiation should have at least one sharply delimited spatial zero point of the radiation power which determines the final resolution of the detected fluorescence radiation. For the STED process, e.g. an excitation radiation source can generate an Airy distribution in the sample with which the sample is transformed from the ground state into the excited state. The depopulation of the excited state takes place by means of a depopulation light source which e.g. has a doughnut- or torus-shaped beam distribution in the sample. The luminescence radiation of the non-depopulated, i.e. non-de-excited, dye molecules is recorded with the help of a detector. The resolution of the microscope is increased by the depopulation above the diffraction limitation which results from the Airy distribution. This is expressed by a reduced point-spread distribution of the high-resolution microscope compared with the conventional microscope.

A further high-resolution microscopy method which is possible within the framework of the invention is discussed in EP 1157297 B1. Non-linear processes are exploited by means of structured illumination. The saturation of the fluorescence serves as non-linearity. Through a structured illumination which is generated by means of an illumination radiation modulator, a shift of the object space spectrum relative to the transmission function of the optical system takes place. Specifically, the shift of the spectrum means that object space frequencies V0 are transmitted at a spatial frequency V0-Vm, wherein Vm is the frequency of the structured illumination. At a given spatial frequency maximally transmissible by the system, this enables the transfer of spatial frequencies of the object lying the shift frequency Vm above the maximum frequency of the transmission function. This approach requires a reconstruction algorithm for image generation and the utilization of several acquisitions for an image. EP 1157297 B1, also fully incorporated by reference herein in respect of the corresponding description of the resolving microscopy method, thus uses a structured wide-field illumination of the sample, wherein a stripe modulation is imposed, for example by an amplitude/phase grating. Fluorescence in the sample is also detected in wide-field. The modulation is now brought into at least three different rotation positions, e.g. 0°, 120° and 240°, and the modulation in each rotation position is shifted into at least three different positions. In each shift of the rotation positions (thus in total at least 9 image positions), the sample is detected in wide-field. The grating further has frequencies as close as possible to the limit frequency, which the optical arrangement used is capable of transmitting. The mentioned spectrum shift then takes place using a Fourier analysis, wherein in particular the $0^{th}$ and $+/-1^{st}$ diffraction order in the images is evaluated. This microscopy method is also called SIM method.

A development of the SIM method can be achieved with a line-type illumination which is perpendicular to the stripe direction of the modulation. There is then a line-type illumination, wherein the stripe structure recurs along the line. The line-type illumination is structured, for its part, by the modulation. The line illumination allows a confocal slit detection and thus, again, an increase in resolution. This method is also abbreviated to SLIM.

An even higher increase in the resolution is obtained when the illumination radiation modulation is carried out on illumination radiation and is so intense that the fluorescence of the sample achieves a saturation into the bright area of the structured illumination. The modulation on the sample then no longer has a sine distribution in respect of the fluorescence, but has still higher harmonics beyond the optical limit frequency because of the saturation effects. This method is also abbreviated to saturated pattern excitation microscopy (SPEM). These three variants of a microscopy which is high-resolution by means of a structured illumination can also be realized in the combination according to the invention or with the microscope according to the invention.

Finally, a further high-resolution method which, independently of laser scanning microscopy, achieves a resolution beyond the diffraction limit is also known from WO 2006127692 and DE 102006021317. All three documents are incorporated by reference in full into the disclosure here in this respect. This microscopy method abbreviated to PAL (Photo Activated Light Microscopy) uses a label substance which can be activated by means of an optical activation signal, with the result that it can be excited to emit particular fluorescence radiation with excitation radiation only in the activated state. Non-activated molecules of the label substance also emit no, or at least no noticeable, fluorescence radiation after irradiation of excitation radiation. In the PAL microscopy method, the activation signal is now applied such that the label molecules activated thereby are spaced apart from neighbouring activated molecules such that they are separated, as measured by the optical resolution of the microscopy, or can be separated subsequently. The activated molecules are thus at least largely isolated. For these isolated molecules, the centre of their radiation distribution caused in resolution-limited manner is then identified and the position of the molecules computationally determined from it with higher precision than the optical imaging itself allows. This increased resolution by computational determination of the centre of the diffraction distribution is also called "superresolution" in the specialist literature. It requires at least some of the activated label molecules to be distinguishable, thus isolated, in the sample with the optical resolution with which the luminescence radiation is detected. For such molecules, the location information can then be achieved with increased resolution.

To isolate individual label molecules, the PAL microscopy method exploits the fact that the probability of a label molecule being activated after receipt of a photon of the activation radiation is the same for all molecules. By adjusting the intensity of the switching signal and thus the number of photons which strike per unit area of the sample, it is thus possible to ensure that the probability of activating label molecules present in a unit area of the sample is so small that there are enough areas in which only distinguishable label molecules emit fluorescence radiation within the optical resolution. The result of a suitable choice of the intensity, i.e. of the photon density, of the switching signal, is that, as far as possible, only label molecules isolated relative to the optical resolution are activated and subsequently emit fluorescence radiation. For these isolated molecules, the centre of the intensity distribution conditional on diffraction and thus the position of the label molecule is then identified computationally with increased resolution. To image the whole sample, the isolation of the label molecules of the partial quantity is repeated by introducing the activation radiation, subsequent excitation and fluorescence radiation imaging until, if possible, all label molecules were contained once in a sub-set and isolated within the resolution of the imaging. The label molecules are de-activated between the successive steps of excitation and renewed activation. This can be achieved either by an additional (preferably optical) de-activation signal or by the label molecules bleaching after the excitation and the emission of fluorescence radiation.

The PAL microscopy method has the advantage that a high spatial resolution is necessary for neither the activation nor the excitation. Instead, both the activation and the excitation can take place in wide-field illumination.

As a result, the label molecules are statistically activated in sub-sets by suitable choice of the intensity of the activation radiation. Therefore, a plurality of frames must be evaluated for the generation of a complete image of a sample in which the positions of all label molecules can be determined computationally with e.g. resolution lying beyond the diffraction limit. The determination of the position of the molecules in the frames takes place by computational procedures, such as are described for example in Egner et al., Biophysical Journal, pp. 3285-3290, volume 93, Nov. 2007.

The combination according to the invention of different high-resolution microscopy methods with one another or with laser scanning microscopy and optionally also additionally with normal wide-field microscopy allows the sample to then be imaged with one of the high-resolution microscopy methods, when a predetermined pattern occurs in the image, in particular after the sample has previously been fixed in respect of changes proceeding in the sample. As the image-acquisition speed is reduced with high-resolution microscopy methods, a rapid image generation can be achieved if a small sample field is selected for the high-resolution microscopy method. In addition, in this way dynamic processes can be examined which actually proceed too quickly relative to the image-acquisition speed of the high-resolution method, by fixing the sample only when the predetermined pattern which displays a particular state of the dynamic development occurs and surveying it in high-resolution. For the fixing, it is preferred to integrate in the microscope a corresponding sample fixing device, such as e.g. for applying a fixing solution by dropping or for quick-freezing. Alternatively, it is also possible to examine an e.g. living sample in high resolution in a resting state and initiate rapid dynamic processes by optical, chemical or other stimuli and then to examine these with one of the faster other microscopy methods, e.g. with LSM or standard wide-field microscopy. Such an observation sequence (high-resolution recording of a resting state, stimulation of a dynamic change, observation of the dynamic change with a lower-resolution and thus faster microscopy method) can also be repeated in a cycle as required.

If standard methods and high-resolution methods are used simultaneously (e.g. LSM and PALM), rapidly changing structures can for example be recorded with the standard method and static objects in high resolution. It is thus provided within the framework of the invention that the different microscopy methods simultaneously record different, optionally overlapping, image fields in the sample. For example, cell membranes can be surveyed statically by means of PALM and, at the same time, vesicles can be recorded highly dynamically by means of a line-scanning LSM with standard resolution.

The different microscopy images are combined according to the invention, in particular brought together or superimposed. This can take place two-dimensionally, three-dimensionally and in each case additionally also over time, wherein the image fields, as already mentioned, can have different sizes. The image fields can overlap fully or partially, but it is also possible to place them next to each other. In order to guarantee a correct relative position of the combined images, image tags are preferably evaluated. These can be obtained by providing the sample beforehand with corresponding structures, e.g. particles, in particular gold particles, which appear in the microscopy images used. The positions of these image tags are evaluated to align and adjust the individual images and taken into account by the control device.

It has been shown that, with the procedure according to the invention, a connection between high-resolution image elements can easily be produced by the inclusion of the image in standard resolution. It is also possible to reveal partially complementary information by using at least two microscopy methods. I f, for example, a TIRF illumination is used for the PAL microscopy method, highly sensitive image information is recorded at the boundary of the cover glass. Because of the greater penetration depth, the parallel use of laser scanning microscopy also obtains information from other sample planes and allows this to be related to the high-resolution detailed information from the PAL microscopy method. It is thereby possible for example to study particular actions in high-resolution on membranes and simultaneously to relate them to processes inside the cell or a united cell structure which have been recorded with standard resolution.

In particular, it is possible to choose the sample section which is imaged with one of the further, in particular one of the high-resolution, microscopy methods in respect of position and size depending on information from one of the other microscopy images.

The procedure according to the invention, however, allows not only the above combination of different microscopy methods for increasing the information on a sample, but also an interaction of the microscopy methods in respect of their performance. For this, it is possible to perform an image evaluation in one of the microscopy images prior to the combination and to derive therefrom at least one control variable for the acquisition of one of the other microscopy images, thus control variables for carrying out one of the other microscopy methods. Possible control variables are: focus position, sample stage position (i.e. position of the sample perpendicular to the optical axis of the objective), choice of objective, spatial distribution of an illumination radiation with STD, ESA or RESOLFT, choice of image section, adjustment of a camera sensitivity, local illumination power of a manipulation radiation which is introduced to influence the fluorescence properties of the sample, transfer of coordinates in respect of image section position, etc.

The combination microscope according to the invention has corresponding devices, with the result that a user has freedom when it comes to combining the described microscopy methods which are then adjusted as operating modes of the control device on the combination microscope.

In particular, a simple adjustment of these operating modes is possible if the illumination radiations of the individual modules are combined via activatable switching means. These switching means can have folding or swivel mirrors which couple the respective illumination radiation into the illumination beam path, thus couple the illumination beam path of the respective module realizing a partial illumination beam path of the microscope to the beam path then to be perceived as main illumination beam path.

It is advantageous for the detection beam path to provide a beam splitter which directs fluorescence radiation excited in the sample to the 2D detector and thus divides the detection beam path in respect of the wide-field detection. In order to have the greatest possible freedom in carrying out the individual microscopy methods, it is advantageous to realize the individual folding or swivel mirrors as well as the beam splitter in the form of dichroic beam splitters which can be exchanged, for example by utilizing a known splitter wheel or several such splitter wheels. With a suitable choice of their spectral properties, the mentioned microscopy methods can thereby also be realized simultaneously by simultaneously illuminating the sample accordingly. In respect of the laser scanning module or a manipulation illumination radiation module, e.g. a coupling-in of a spot scanner in the laser scanning microscope or in the manipulation illumination radiation module to a remainder of the illumination beam path which guides wide-field or line-type illumination takes place. It is thus possible to also realize the corresponding switching means as achromatic beam splitters, such as are described for example in US 2008/0088920, the disclosure of which is incorporated by reference here in full in this respect.

For the SIM, SLIM and SPEM microscopy methods, a rotation of the direction of modulation of the structured illumination is necessary, as has already been described at the beginning. The rotation can be realized particularly simply if an image-field rotator is arranged downstream of the modulator which, for the realization of these microscopy methods, lies in the common section of second and third illumination beam path. This can be realized for example by an Abbe-Koenig prism. This downstream image-field rotator is particularly advantageous for the SLIM microscopy method, as the perpendicular position of stripe modulation and linear illumination need then be adjusted only once and a tracking, which would otherwise be necessary in the case of a rotation of the modulator, is dispensed with. Of course, the modulator itself can also be rotated, e.g. by a rotatable strip grating or a suitably driven modulator (e.g. a DMD or LCD).

The microscope according to the invention has a particularly simple structure if the individual partial illumination beam paths of the modules are combined cascade-like to a main illumination beam path which is then coupled in at the beam splitter for the detection beam path. The individual partial illumination beam paths are thus coupled into the total illumination beam path at different points, for example by the mentioned switching means. Switching means are of course not necessary when the activation or de-activation of the individual partial illumination beam paths can take place in another way, for example in the affected modules themselves.

It is understood that the features named above and still to be explained below can be used not only in the given combinations, but also in other combinations or alone, without departing from the framework of the present invention.

BRIEF DESCRIPTION OF THE DRAWINGS

The invention is explained in further detail below by way of example using the attached drawings which also disclose features essential to the invention. There are shown in.

DETAILED DESCRIPTION

Figure 1:
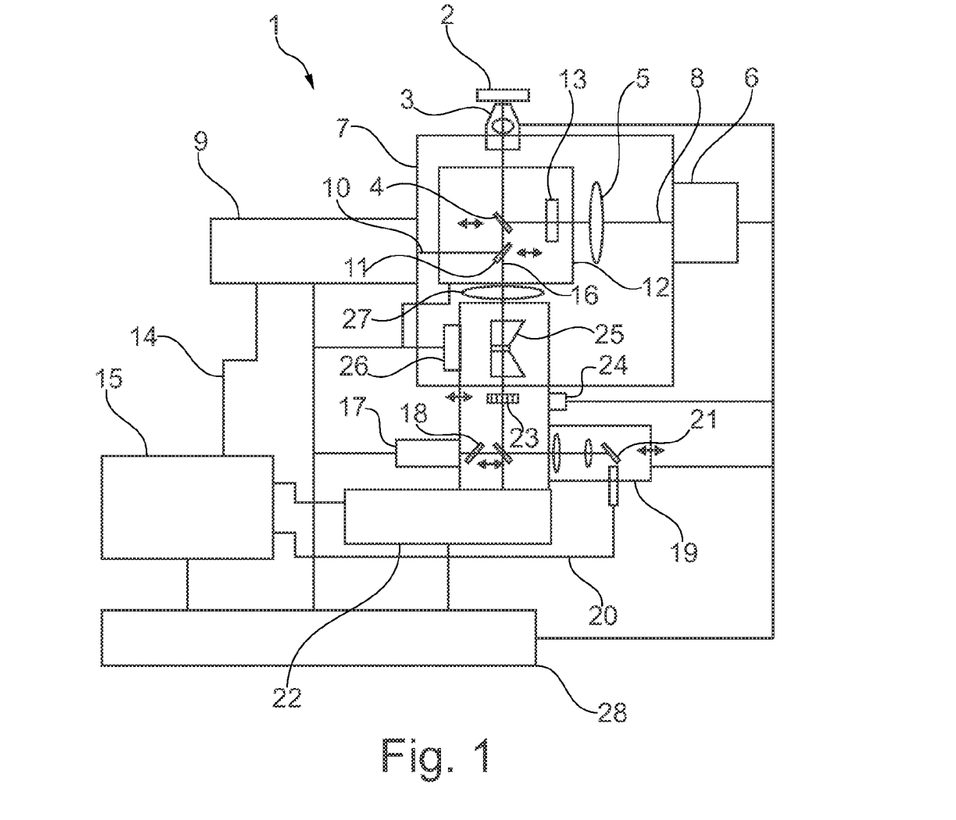
FIG. 1 is a schematic representation of a combination microscope.

In FIG. 1, a microscope 1 is represented which can carry out standard microscopy methods, i.e. microscopy methods the resolution of which is diffraction-limited, simultaneously with high-resolution microscopy methods, i.e. with microscopy methods the resolution of which is increased beyond the diffraction limit. The microscope 1 is modular in structure, and it is described in a comprehensive expansion stage to better illustrate the invention. However, a reduced structure with few modules is also possible. The modular structure is also not necessary; a one-piece or non-modular design is likewise possible. The microscope 1 of this example of FIG. 1 is constructed on the basis of a conventional laser scanning microscope and senses a sample 2.

It has an objective 3 through which the radiation passes for all microscopy methods. Via a beam splitter 4, the objective 3 images the sample together with a tube lens 5 onto a CCD detector 6 which is an example of a generally possible 2D detector. In this respect, the microscope 1 has a conventional light microscope module 7, and the beam path from the sample 2 through the objective 3 and the tube lens 5 to the CCD detector 6 corresponds to a conventional wide-field detection beam path 8. The beam splitter 4 is, as indicated by the double arrow in FIG. 1, exchangeable in order to be able to switch between beam splitters with different dichroic properties or achromatic beam splitters according to US 2008/0088920.

Also connected into the beam path to the objective 3 is a laser scanning module 9 the LSM illumination and detection beam path of which is coupled into the beam path to the objective 3 via a switching mirror 11 which also has beam splitter functions. The beam path from the switching mirror 11 to the objective 3 through the beam splitter 4 is thus a beam path in which illumination beam path and detection beam path are combined. This applies both in respect of the laser scanning module 9 and in respect of the wide-field detection beam path 8 since, as is still to be explained, illumination radiation which realizes microscopy methods together with the wide-field detection beam path 8, i.e. the CCD detector 6, is also coupled in at the switching mirror 11.

The switching mirror 11 and the beam splitter 4 are combined into a beam splitter module 12, whereby there is the possibility of exchanging the switching mirror 11 and the beam splitter 4 depending on use. This is shown by double arrows. An emission filter 13 which lies in the wide-field detection beam path 8 and suitably filters the spectral proportions which can propagate through the wide-field detection beam path 8 is further provided in the beam splitter module 12. Of course, the emission filter 13 in the beam splitter module 12 is also exchangeable.

The laser scanning module 9 obtains laser radiation necessary for the operation via an optical fiber 14 from a laser module 15.

In the design represented in FIG. 1, a collection illumination beam path 16 through which illumination radiation passes for different microscopy methods is coupled in at the beam splitter module 12, more precisely at the switching mirror 11. Different partial illumination beam paths of individual illumination modules are coupled into this main illumination beam path 16. For example, a wide-field illumination module 17 couples wide-field illumination radiation into the main illumination beam path 16 via a switching mirror 18, with the result that the sample 2 is wide-field illuminated via a tube lens 27 and the objective 3. The wide-field illumination module can have for example an HBO lamp. A TIRF illumination module 19 which realizes a TIRF illumination for suitable positions of the switching mirror 18 is provided as a further illumination module. For this, the TIRF illumination module 19 receives radiation from laser module 15 via an optical fiber 20. The TIRF illumination module 19 has a mirror 21 which can be moved longitudinally. The illumination beam which is emitted by the TIRF illumination module 19 is moved perpendicular to the main propagation direction of the emitted illumination beam by the longitudinal shift, whereby the TIRF illumination is consequently incident on the objective 3 at an adjustable angle to the optical axis of the objective 3. In this way, the necessary angle of the total reflection at the cover glass can be easily guaranteed. Of course, other means for effecting this angle adjustment are also suitable. The TIRF illumination module 19 can also operate as a wide-field illumination source by adjusting the mirror 21 such that the illumination beam is incident on the optical axis.

The illumination beam path of a manipulator module 22 which likewise receives radiation from the laser module 15 via an optical fiber, not identified in detail, and guides a spot or line-type beam distribution in scanning manner over the sample 2 is further coupled to the main illumination beam path. The manipulator module 22 thus substantially corresponds to the illumination module of a laser scanning microscope, and therefore the manipulator module 22 can also be operated combined with the detector of the laser scanning module 9 or the wide-field detection by the CCD detector 6.

A strip grating 23 which lies in an intermediate image plane of the illumination beam path and the grating constant of which lies below the limit frequency which can be transmitted into the sample 2 with the microscope 1 is further provided as a radiation modulator in the main illumination beam path 16. The grating 23 brings about a stripe modulation of the illumination radiation incident on it. The grating 23 can be shifted transversely to the optical axis of the main illumination beam path 16 and can also be swivelled out of the beam path. A corresponding shift drive 24 is provided for this.

An image-field rotator 25 which is rotated by a rotator drive 26 further sits downstream of the grating in illumination direction in the collection illumination beam path 16. The image-field rotator can be for example an Abbe-Koenig prism.

The modules and drives as well as detectors of the microscope 1 are all connected to a control device 28 via lines, not identified in detail. This connection can take place for example via a data and control bus. The control device 28 drives the microscope 1 into different operating modes.

The control device 28 is adapted to have the microscope 1 perform standard microscopy, i.e. wide-field microscopy (WF), laser scanning microscopy (LSM) and also total internal reflection fluorescence microscopy (TIRF), and to combine this with high-resolution microscopy methods, such as in the PALM, SIM, SLIM, SPEM, STED, RESOLFT mentioned at the beginning, and also to combine these with one another. The microscope 1 of FIG. 1 essentially has two modules suitable for laser scanner illumination, namely the laser scanning module 9 as well as the manipulator module 22. Of course, other combinations are also possible. These modules are coupled onto the sample 2 via tube lenses and the objective 3. The manipulator module 22 contains only the excitation part of a laser scanning module, i.e. without detection. The sample can thereby be illuminated spot-by-spot and the illumination spot scanned over the sample 2. A switching unit, e.g. a switching lens or cylindrical lens with which a switching between a spot-by-spot and a line-type illumination takes place, is also preferably located in the manipulator module 22. This line-type illumination is particularly advantageous when the grating 23 which is located in an intermediate image of the main illumination beam path 16 is swivelled in and lies perpendicular to the line of the line-type illumination. The SLIM microscopy method can then be easily realized by means of the manipulator module 22.

As an alternative to the grating 23, a variably adjustable stripe modulator or a DMD can also be used to generate a structured illumination in the sample 2. Of course, the shift drive 24, as well as the ability of the grating 23 to swivel in/out, is then no longer necessary.

The image-field rotator 25 allows the structured illumination which is generated by the grating 23 (or the elements replacing this) to rotate about the optical axis of the main illumination beam path 16, with the result that the structured illumination lies at different angles in the sample 2. Thus, SIM, SLIM or SPEM microscopy can be carried out with the microscope 1 by operating the manipulator module 22 or the wide-field illumination module 17, in each case in combination with suitable adjustment of the grating 23 by the control device 28. Of course, the switching mirror 18 is then to be brought into the suitable position.

When the grating 23 is swivelled out, a standard wide-field illumination by the wide-field illumination module 17 or a standard TIRF illumination by the TIRF illumination module 19 can be effected.

To switch between the individual operating modes, the switching mirrors 18 and 11 as well as the beam splitter 4 are suitably adjusted. For this, folding or swivel mirrors can be used in the implementation, with the result that a switching can be effected sequentially between the operating types. Alternatively, dichroic mirrors which enable a simultaneous operation of the different modules are also possible.

The beam splitter 4 is preferably designed as a dichroic beam splitter the spectral properties of which are adjustable such that spectral proportions of fluorescence emission of tagging molecules which are to be detected with the help of the CCD detector 6 enter the wide-field detection beam path 8 and the remaining spectral components are transmitted to the greatest possible extent. To increase the flexibility in respect of the usability of tagging molecules with different emission characteristics, several different beam splitters 4 and emission filters 13 are arranged exchangeable in the beam splitter module 12, e.g. on a filter wheel.

The combination of LSM and PALM using dichroic beam splitters or switching mirrors 4, 11 and 18 is described below by way of example. For example, the sample 2 is provided with an Alexa 543 label which can be excited at a wavelength of 543 nm and emits fluorescence radiation above 550 nm. For the PAL microscopy, an EOSFP label is used which can be activated with radiation of 405 nm, can be excited at 488 nm and the fluorescence radiation of which is detected in the range between 490 and 540 nm. For this operation mode, the grating 23 is swivelled out and the TIRF illumination module 19 is adjusted such that TIRF illumination takes place with 488 nm. The activation of the label substance EOSFP is effected by utilizing the manipulator module 22 which, for this, illuminates the sample 2 with laser radiation of 405 nm. The following parameters are set for the individual beam splitters or switching mirrors.

| Element | 4 | 11 | 18 | 13 |
|---|---|---|---|---|
| Transmission | <490; >550 | <540 | <480 | 490-550 |
| Reflection | 490-550 | >540 | >480 | |

All of the wavelength data given above are in nm.

In a further type of operation, SIM is combined with PALM, wherein the image acquisition is effected sequentially. For this, the sample 2 is provided for example with a DAPI label substance which can be excited at 405 nm and the fluorescence radiation of which lies between 420 and 520 nm. For the PALM method, a tdEOS label of the sample is used which can be activated at 488 nm, can be excited at 561 nm and can be detected above 565 nm. The activation of this label is effected by the TIRF illumination module 19. For the acquisition of the PALM image, the grating 23 is swivelled out and the TIRF illumination module 19 activated. For the acquisition of the SIM image, the grating 23 is swivelled in and the sample wide-field illuminated from the wide-field illumination module 17. The beam splitters/switching mirrors are then set as follows:

| Element | | 4 | 11 | 18 | 13 |
|---|---|---|---|---|---|
| SIM | Transmission | <565 | Swivelled out | Mirror | >565 |
|  | Reflection | >565 | | | |
| PALM | Transmission | <420 | | | >420 |
|  | Reflection | >420 | | | |

All of the wavelength data given above are in nm.

Figure 2:
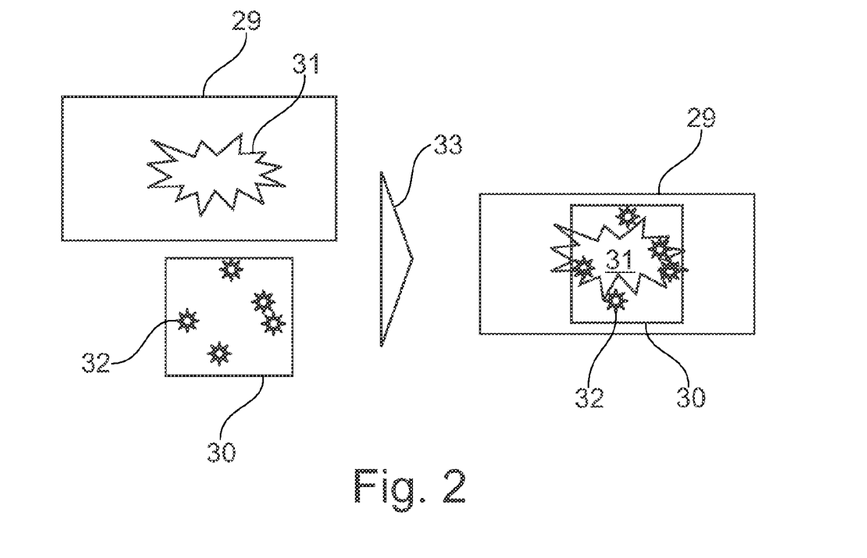
FIG. 2 schematically depicts the superimposition of different images which have been obtained with the combination microscope of FIG. 1.

FIG. 2 schematically shows the superimposition of the different microscopy images which are obtained with the help of the combination microscope 1 of FIG. 1. The microscopy image 29 originates from a standard microscopy method, for example from normal fluorescence microscopy using the wide-field illumination source 17 and wide-field detection. The microscopy image 30, on the other hand, originates from a high-resolution method, for example a SIM or PAL microscopy. FIG. 2 illustrates that the high-resolution image 30 covers a very much smaller object field of the sample 2 than the microscopy image 29. There are structures 31 in the microscopy image 29; structures 32 are present in the high-resolution microscopy image 30. The control device 28 now superimposes the respective images into a total image in a superimposition procedure 33 symbolized by an arrow. The superimposition can take place two-dimensionally, three-dimensionally and also over time for both variants in each case. FIG. 2 shows a two-dimensional representation by way of example. FIG. 2 further schematically shows that a higher-resolution microscopy image 30 is combined with a lower-resolution microscopy image 29, i.e. that the combination of two microscopy methods with different resolutions result in a total image. It is to be seen in FIG. 2 that only with the help of the lower-resolution microscopy image 29 a context between the high-resolution details of the higher-resolution microscopy image 30 can be produced.

The microscopy image 29 can be generated for example by means of SIM or LSM, wherein label molecules of a first type contribute to the imaging, e.g. FITC or Alexa. The higher-resolution image can originate for example from PAL microscopy and delivers detailed information for another label dye, e.g. DRONPA. The superimposition procedure allows partly complementary information of the methods to be combined in the composed image. For example, a PALM with TIRF illumination senses information only for the boundary between cover glass and sample 2. If an LSM microscopy image is acquired in parallel, information from other sample planes can also be obtained due to the greater penetration depth, and this can be related to the high-resolution microscopy image and its detailed information.

Under controlling of the control device 28, it is thus possible to study particular sequences in high-resolution, e.g. on membranes, and at the same time relate them to other processes, e.g. within a cell or a united cell structure. As the image-acquisition rate is lower with high-resolution methods than with methods with lower resolution or standard resolution, dynamic processes can be examined only to a limited degree, or not at all, with high-resolution methods. Therefore, particular fixings of the sample 2 in order to stop a shift of the sample or diffusions in the sample 2 are also known. With the help of the microscope 1, dynamic sequences in the sample 2 can now first be examined by means of microscopy methods which have a comparatively lower resolution, but are faster for it, and the sample 2 can be fixed and surveyed in high resolution when a particular event occurs in the sample 2 which reveals itself e.g. in a predetermined pattern in the correspondingly generated microscopy image. For this, it is preferred to integrate sample fixing devices into the microscope 2, for example a device for dropping a fixing solution on the sample 2 or quick-freezing the sample 2. Living cells can also be examined in high resolution in a resting state and rapid, dynamic processes can then be initiated by optical (e.g. by means of the manipulator module 22), chemical or other stimuli and these processes can be observed with lower-resolution microscopy methods (e.g. with LSM or WF). This observation sequence (high-resolution microscopy of a resting state—stimulation of a dynamic process—lower resolution of the dynamic change arising) can also be repeated cyclically as needed. In an embodiment the control device 28 represents the microscopy images superimposed in a four-dimensional composite image.

If standard methods (LSM and WF) and high-resolution methods (SIM, SLIM, STEM, PALM, STED, RESOLFT) are used simultaneously, for example, partial areas of the sample 2 in which rapid changes are to be expected can be acquired in low resolution and with higher image sample frequency and static partial areas in the sample 2 in high resolution and with lower image sample frequency. The combinations of the microscopy methods can thus also take place at the same time in the sample and in particular record different fields of view of the object field in the sample 2. An example of this is the labelling of static cell membranes with EOSFP and surveying them by means of PALM and the simultaneous rhodamine colouring of cell vesicles and their representation by means of a confocal line scanner (line-scanning LSM). The vesicles then appear in the composite image with high time resolution (e.g. 200 nm spatial and 10 ms time resolution) before a highly resolved cell membrane (e.g. 20 nm resolution). When the images are superimposed, in principle a balancing or an adjustment of the individual microscopy images 29 and 30 can be effected by appropriately aligning the structure 32 of the higher-resolution image 30 to appropriate structures 31 of the lower-resolution image 29 during the superimposition. For this, so-called adjustment structures can also be introduced into the sample 2, e.g. fluorescent gold particles. With the help of these adjustment structures, the adjustment of the position of the microscopy images then is effected before their superimposition to form the composite image.

Where the superimposition of two microscopy images is described here, this is of course to be understood purely by way of example. Of course, a larger number of images can also be superimposed.

Figure 3:
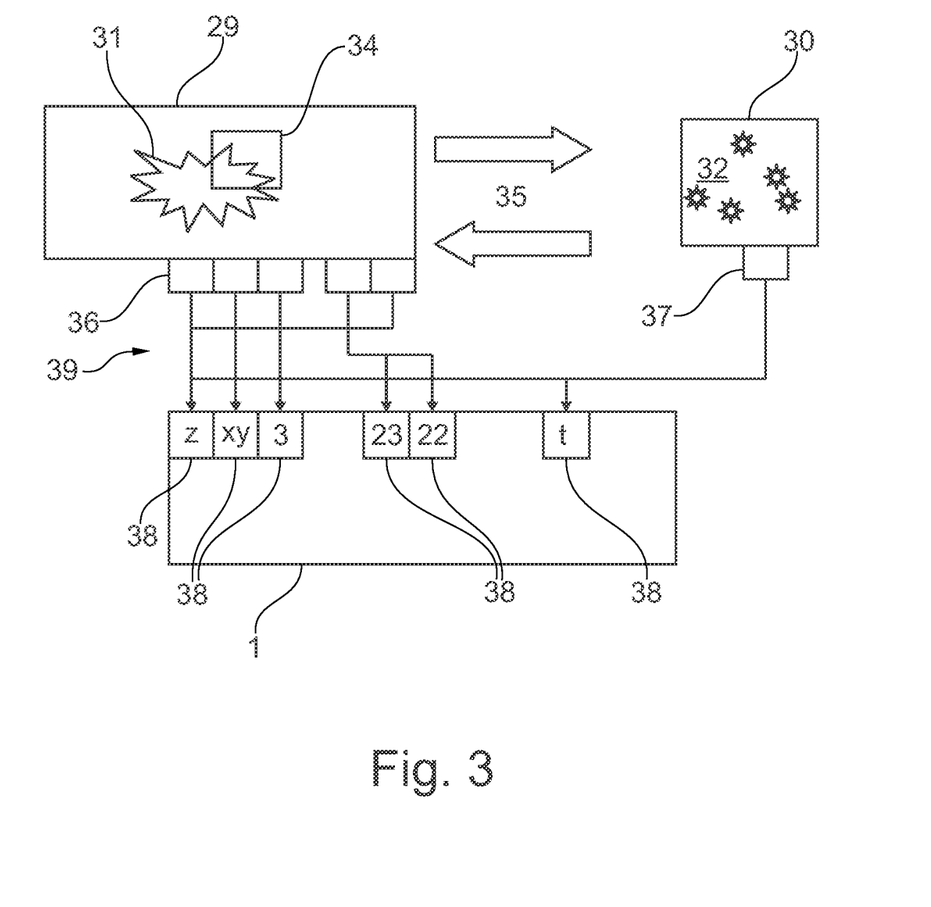
FIG. 3 is a schematic representation for controlling the combination microscope of FIG. 1.

However, the different microscopy methods carried out sequentially or simultaneously give not only increased image information, but allow also an improvement in the image-acquisition conditions of one microscopy method by utilizing information from another microscopy method. FIG. 3 schematically shows a closed-loop adjustment in which information from a lower-resolution microscopy image 29 and/or information from a higher-resolution microscopy image 30 are utilized to exert an influence 35. The evaluation of the lower-resolution microscopy image 29 can be effected in the whole image or also in an image part 34, for example an image part 34 which corresponds to the object field which is imaged in the higher-resolution microscopy image 30. In one or both of the microscopy images, a feature analysis 36 or 37 to effected which is illustrated schematically in FIG. 3. Correcting variables for the operation of the microscope 1 are derived from this feature analysis, wherein the effects 39 on control variables 38 of the microscope 1 can also result in a cross-influencing whereby changes in control variables 38 which have an effect on the acquisition of the higher-resolution microscopy image 30 are derived from the lower-resolution microscopy image 29 and vice versa. For example, the contrast can be determined from the lower-resolution microscopy image 29 and the position of the focus position z corrected from it. A correction of a sample drift xy can be effected by determining the position of a structure of the sample 2.

Structure sizes can be used to choose the proper objective 3. A brightness analysis of the sample and thus an analysis of a dye concentration can be used to select an appropriate grating 23 or to set the illumination power of the manipulator 22. A SLIM illumination can also be realized or the sensitivity of the CCD detector 22 or a camera embodying the 2D detector of the wide-field detection can be adjusted.

The establishment of an image view of interest 34 can also be used to set the local illumination power of the manipulator module 22. A coordinate transfer x, y, z can also be effected in order to determine or preset the image field 34 for the high-resolution microscopy image 29.

A structure can in turn be analyzed from the higher-resolution microscopy image 30 and a corresponding additional imaging can be effected through the lower-resolution microscopy image 30 or the sample can be excited by the manipulator module 22 at suitable points with radiation for the manipulation of the fluorescence properties.

Figure 4:
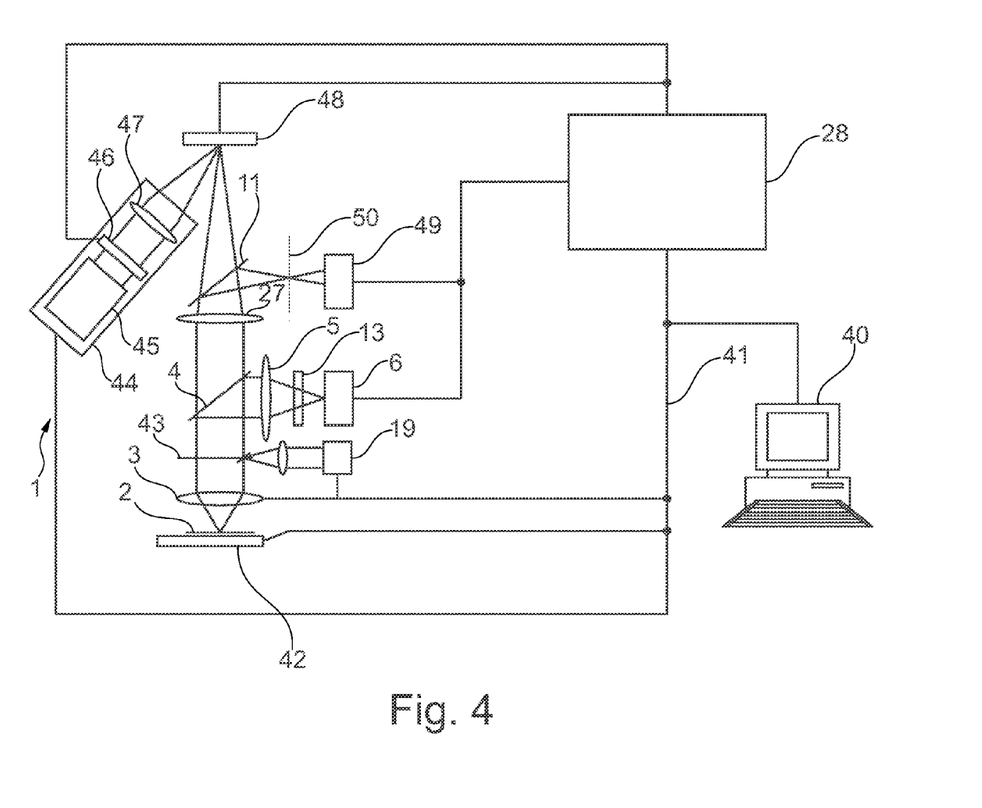
FIG. 4 is a further combination microscope similar to that of FIG. 1.

FIG. 4 schematically shows a further embodiment of the combination microscope 1, wherein already-described modules are provided with the same reference numbers and therefore need not be explained again here. However, it may be pointed out that the of the individual modules, in particular of the laser scanning module 9, of the manipulator module 22, of the wide-field illumination module 17 as well as of the TIRF module 19, can also be arranged at other locations in the illumination beam path or the illumination and detection beam path. This is shown by way of example in FIG. 4 for the TIRF module 19 which now couples the corresponding illumination radiation into a pupil 43 between the beam splitter 4 and the objective 3.

A display 40 or a corresponding computer with a display 40 which is also connected to a data and control network 41 via which the control device 28 is connected to the individual modules of the combination microscope 1 is further shown by way of example in FIG. 4.

A sample stage 42 on which the sample 2 can be moved under control of the control device 28 is also shown in FIG. 4. Such a sample stage is of course, like all other details of FIG. 4 as well, also possible in the microscope of FIG. 1.

The laser scanning module 9 of FIG. 1 is shown in FIG. 4 with several components. A laser device 44 comprises a laser 45 which acts on a phase modulator 46 driven by the control device 28. A lens system 47 then focuses the radiation onto a DMD 48. For the detection arm of the LSM module 9, an LSM detector 49 is shown by way of example in FIG. 4, as well as a confocal diaphragm located in an intermediate image plane 50.

With the combination microscope 1 of FIG. 1 or 4, it is possible to record, sequentially or simultaneously, LSM microscopy images and PALM microscopy images and to adjust the acquisition of the PALM microscopy images online by means of information which has been obtained from the LSM microscopy image.

For this, in a first step an LSM image of the sample 2 is recorded and shown on the screen 40. Regions of particular interest (ROIs) can now be selected by a user alone, supported by the computer or automatically from a microscopy image and the control of the activation radiation from the laser module 44 is influenced accordingly. For this, the DMD 48 which is illuminated over its whole surface by laser radiation from the laser 45 is used. The individual mirrors of the DMD are now set such that only the selected ROIs are illuminated and an optical activation of the dye (e.g. DRONPA or EOSFP) is thus carried out only in these regions. The remaining mirrors of the DMD remain in a switched-off position, and the radiation directed onto them is absorbed in a beam trap (not shown). Of course, the switched-on mirrors can also be time-modulated in order to continuously attenuate the activation power. The activation power can thereby be efficiently matched, particularly advantageously for the PAL method, to the molecule concentration with the result that, regardless of the local marker concentration, the activated molecules are located at a distance greater than the optical resolution of the microscope 1. Thus, the sample 2 can be surveyed particularly quickly, in particular as the activation can be suitably set by the concentration of the molecules in the sample previously known from the lower-resolution microscopy image or simultaneously identified in the lower-resolution microscopy image. A local adjustment is particularly advantageous if strong local concentration changes occur, e.g. bright areas are present next to faintly coloured areas. Locally different bleaching of tagging substances, which can occur e.g. because of structural variations in the sample 2, can further lead to local concentration changes which can now be particularly advantageously balanced with the activation adjustment.

Alternatively or additionally, in the case of an activation in pre-defined ROIs by means of the phase modulator 46, the ROI pattern can be imaged preformed onto the whole DMD 48 which then still carries out only a fine tuning. Thus the power of the laser 45 is almost completely used to activate marker molecules in the sample 2. For this, the phase modulator 46 is arranged in a pupil plane before the DMD 48 (seen from the laser 45) and is located at a distance to the focal lengths of the lens system 47 (which can also be realized by a lens). The DMD 48 is in turn located at the distance f after the lens system 47. Alternatively, the DMD 48 can also be omitted if for example the ROI selection takes place through the phase modulator 46 and the intensity of the laser source 45 is globally adjusted, e.g. by an intensity modulator downstream of the laser or a direct intensity modulation of the laser 45.

Where combinations or evaluations of microscopy images have been discussed here, these are to be understood purely by way of example and not as limiting the microscopy method on which the mentioned images are based. Rather, the described evaluations, combinations, control influencings, etc. can also be used with others of the mentioned microscopy methods.

The invention claimed is:

1. A method for generating an image of a sample by microscopy methods which provide different spatial resolutions, wherein at least two of the following microscopy methods are combined:
   a first microscopy method including
      exciting the sample to luminescence by structured line-type or wide-field illumination;
      if structured line-type illumination is used, rotating a structuring and shifting the structuring several times for each rotation position, wherein at least three rotation positions and at least three shift positions per rotation position are realized;

imaging the luminescent sample onto a 2D detector with a predetermined optical resolution for each combination of rotation position and shift position; and generating a first microscopy image with spatial resolution increased beyond the predetermined optical resolution from thus-obtained images by a computational processing comprising Fourier analysis, a second microscopy method including:

labelling the sample with label molecules which can be excited to emit particular luminescence radiation only after being activated by a switching signal;

applying the switching signal to the sample such that only a sub-set of the label molecules present in the sample are activated, wherein there are partial areas in the sample in which activated label molecules have a distance to their closest neighbouring activated label molecules which is greater than or equal to the predetermined optical resolution;

exciting the activated molecules to emit luminescence radiation;

imaging the sample emitting luminescence radiation onto the 2D detector with the predetermined optical resolution;

analyzing the image; and generating image data from the image which give geometric locations of the label molecules emitting luminescence radiation with a local resolution increased above the predetermined optical resolution; and generating a second microscopy image from the image data, a third microscopy method including generating a third microscopy image by application of laser scanning microscopy, and combining at least two obtained microscopy images from the first, second and third microscopy images into a composite image.

2. The method according to claim 1, wherein combining the at least two obtained microscopy images into a composite image, further comprises superimposing the at least two obtained microscopy images.

3. The method according claim 2, further comprising determining a position of the microscopy images relative to each other before the superimposition of the microscopy images and superimposing the microscopy images position-adjusted.

4. The method according to claim 1, wherein a first step includes generating a microscopy image of the sample with one of the first to third microscopy methods; a second step includes scanning the microscopy image for a predetermined pattern and, if the predetermined pattern is discovered, performing a third step including generating a further microscopy image with at least one of the other microscopy methods; and further comprising fixing the sample regarding processes taking place in the sample.

5. The method according to claim 4, wherein fixing the sample occurs after the second and before the third step.

6. The method according to claim 4, further comprising, before the third step, selecting a sample view depending on the pattern and in the third step generating the further microscopy image only for the sample view.

7. The method according to claim 1, further comprising first generating a microscopy image with one of the first to third microscopy methods, carrying out an image evaluation in the microscopy image and deriving at least one control variable for the acquisition of at least one of the other microscopy images, wherein the control variables comprise:

focus position,
sample stage adjustment,
choice of objective, and
choice of image view.

8. The method according to claim 1, wherein prior to combining the microscope images into the composite image, an alignment of a higher resolved image to a lower resolved image is performed by adjusting the images to each other on basis of structures occurring in the images.

9. A combination microscope, adapted for the microscopy of a sample with at least two microscopy methods differing in their resolution, wherein the microscope comprises:

an objective which senses the sample for all microscopy methods a detection beam path and at least one illumination beam path which at least partially coincide and both pass through the objective;

a microscope module connected to the detection beam path which has a tube lens and a 2D detector and, the tube lens together with the objective, imaging the sample onto the 2D detector;

a wide-field illumination module connected to the illumination beam path for wide-field illumination of the sample through the objective, wherein the wide-field illumination module is structured to emit illumination radiation in at least two different wavelength ranges; and an illumination radiation modulator located in the illumination beam path downstream of the wide-field illumination module in an illumination direction and which is controllably activatable and de-activatable in the illumination beam path and imposes in an activated state a stripe modulation to the illumination radiation, wherein the illumination radiation modulator is shiftable such that the stripe modulation can be shifted perpendicular to an optical axis of the illumination beam path, and further comprising a controllable rotation device with which either the stripe modulation is rotatable about the optical axis of the illumination beam path or ray beams that have passed through the activated illumination radiation modulator and are thereby provided with the stripe modulation are rotatable in the illumination beam path about the optical axis of the illumination beam path, and a control device which is connected to the microscope module, the wide-field illumination module, the illumination radiation modulator and the rotation device and drives the microscope into a first and a second operating modes;

wherein in the first operating mode the control device is operable to activate the illumination radiation modulator and to drive the illumination radiation modulator together with the rotation device as well as to read the 2D detector and to process data delivered by the 2D detector, to generate a first microscopy image with spatial resolution increased beyond a predetermined optical resolution from output of the 2D detector by a computational processing comprising Fourier analysis, and wherein in the second operating mode the control device is operable to de-activate the illumination radiation modulator and to drive the wide-field illumination module successively to emit the illumination radiation in the at least two different wavelength ranges as well as to read the 2D detector and to process data delivered by the 2D detector, to analyze the process data of the 2D detector and to generate data second microscopy image which give geometric locations of label molecules emitting luminescence radiation with a local resolution increased above the optical resolution.

10. The microscope according to claim 9, further comprising a manipulation illumination radiation module also driven by the control device which manipulation illumination radiation module is connected to be activated in the illumination beam path, to illuminate the sample in spot- or line-type-scanning manner with manipulation illumination radiation for manipulation of fluorescence properties of the sample.

11. The microscope according to claim 10, wherein manipulation illumination radiation emitted by the manipulation illumination radiation module also passes through the illumination radiation modulator, when the illumination radiation modulator is activated.

12. The microscope according to claim 10, further comprising a switching device also driven by the control device that connects and disconnects the manipulation illumination module.

13. The microscope according to claim 12, wherein the switching device comprises at least one folding or swivel mirror.

14. The microscope according to claim 9, further comprising a TIRF illumination module also driven by the control device connected to be activated in the illumination beam path, to illuminate the sample through the objective at an angle such that total reflection is effected in a cover glass arranged on the sample.

15. The microscope according to claim 9, further comprising a beam splitter which guides fluorescence radiation excited in the sample to the 2D detector in the detection beam path.

16. The microscope according to claim 9, wherein the rotation device comprises an image-field rotator.

17. The microscope according to claim 9, wherein the image-field rotator comprises an Abbe-Koenig prism.

18. The microscope according to claim 9, further comprising a digital micromirror device, driven by the control device in an intermediate image plane of the illumination beam path, the mirrors of the digital micromirror device directing illumination radiation to a beam trap when in an off-position and onto the objective when in an on-position.

19. The microscope according to claim 18, further comprising a phase modulator arranged in the illumination beam path and in front of the digital micromirror device.

* * * * *